United States Patent
Austin et al.

(10) Patent No.: US 9,849,216 B2
(45) Date of Patent: Dec. 26, 2017

(54) SYSTEMS AND METHODS FOR DELIVERING A MEDICAMENT

(75) Inventors: Gene Edward Austin, Bartlett, TN (US); Sied W. Janna, Memphis, TN (US); James K. Rains, Cordova, TN (US); John Rose, Collierville, TN (US); Lee Whitehurst, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1282 days.

(21) Appl. No.: 12/281,495

(22) PCT Filed: Mar. 2, 2007

(86) PCT No.: PCT/US2007/005533
§ 371 (c)(1),
(2), (4) Date: Dec. 11, 2009

(87) PCT Pub. No.: WO2007/103276
PCT Pub. Date: Sep. 13, 2007

(65) Prior Publication Data
US 2010/0094195 A1    Apr. 15, 2010

Related U.S. Application Data

(60) Provisional application No. 60/778,778, filed on Mar. 3, 2006.

(51) Int. Cl.
*A61N 1/30* (2006.01)
*A61L 27/54* (2006.01)
(Continued)

(52) U.S. Cl.
CPC ............ *A61L 27/54* (2013.01); *A61K 9/0009* (2013.01); *A61K 9/0024* (2013.01); *A61L 27/34* (2013.01);
(Continued)

(58) Field of Classification Search
CPC .... A61L 31/16; A61L 27/54; A61L 2300/602; A61L 2420/08
(Continued)

(56) References Cited

U.S. PATENT DOCUMENTS 3,531,561 A   9/1970   Trehu
3,636,956 A   1/1972   Schneider
(Continued)

FOREIGN PATENT DOCUMENTS

DE   202006009013   8/2006
EP   0062459   10/1982
(Continued)

OTHER PUBLICATIONS

International Search Report and Written Opinion for International Application No. PCT/US2012/046694, dated Jan. 28, 2013.
(Continued)

*Primary Examiner* — Phillip Gray
(74) *Attorney, Agent, or Firm* — Fish & Richardson P.C.

(57) ABSTRACT

A medicament containment device (106) is provided containing a medicament (114) and is associated with an implant, such as an orthopedic implant (102). The medicament containment device (106) can degrade upon exposure to energy, such as energy (112) from an energy source (110). The orthopedic implant (102), including the medicament containment device is implanted or inserted into an environment (100) such as a patient's body. The energy source (110) can be used outside the patient's body, but in proximity to the orthopedic implant (102), to apply energy (112) to the medicament containment device (106). Upon exposure to the energy (112), the medicament containment device (106) can degrade and release the medicament (114) into the environment (100). The medicament (114) can kill and/or
(Continued)

disrupt bacterial cells (108) or other infectious cells that form in proximity to the orthopedic implant (102).

21 Claims, 8 Drawing Sheets (51) Int. Cl.
A61K 9/00 (2006.01)
A61L 27/34 (2006.01)
A61L 27/50 (2006.01)

(52) U.S. Cl.
CPC ......... A61L 27/50 (2013.01); A61L 2300/608 (2013.01)

(58) Field of Classification Search
USPC ............... 604/20–22, 501, 890.1–892.1, 131
See application file for complete search history.

(56) References Cited

U.S. PATENT DOCUMENTS

| | | |
|---|---|---|
| 3,676,401 A | 7/1972 | Henry |
| 3,736,646 A | 6/1973 | Schmitt et al. |
| 3,797,499 A | 3/1974 | Schneider |
| 4,137,921 A | 2/1979 | Okuzumi et al. |
| 4,181,983 A | 1/1980 | Kulkarni |
| 4,281,664 A | 8/1981 | Duggan |
| 4,361,153 A | 11/1982 | Slocum et al. |
| 4,438,253 A | 3/1984 | Casey et al. |
| 4,513,743 A | 4/1985 | van Arragon et al. |
| 4,523,591 A | 6/1985 | Kaplan et al. |
| 4,539,981 A | 9/1985 | Tunc |
| 4,576,158 A | 3/1986 | Boland |
| 4,636,215 A | 1/1987 | Schwartz |
| 4,840,632 A | 6/1989 | Kampner |
| 4,858,603 A | 8/1989 | Clemow et al. |
| 4,938,763 A | 7/1990 | Dunn et al. |
| 4,950,258 A | 8/1990 | Kawai et al. |
| 4,952,928 A | 8/1990 | Carroll et al. |
| 4,990,161 A | 2/1991 | Kampner |
| 5,049,591 A | 9/1991 | Hayashi et al. |
| 5,108,755 A | 4/1992 | Daniels et al. |
| 5,110,852 A | 5/1992 | Gogolewski et al. |
| 5,192,301 A | 3/1993 | Kamiya et al. |
| 5,201,738 A | 4/1993 | Scott et al. |
| 5,201,771 A | 4/1993 | Belykh et al. |
| 5,258,422 A | 11/1993 | Chang et al. |
| 5,275,601 A | 1/1994 | Gogolewski et al. |
| 5,294,395 A | 3/1994 | Broyer |
| 5,309,919 A | 5/1994 | Snell et al. |
| 5,330,477 A | 7/1994 | Crook |
| 5,333,624 A | 8/1994 | Tovey |
| 5,337,747 A | 8/1994 | Neftel |
| 5,383,931 A | 1/1995 | Hehli et al. |
| 5,383,935 A | 1/1995 | Shirkhanzadeh |
| 5,407,445 A | 4/1995 | Tautvydas et al. |
| 5,417,712 A | 5/1995 | Whittaker et al. |
| 5,423,334 A | 6/1995 | Jordan |
| 5,437,918 A | 8/1995 | Taniguchi et al. |
| 5,441,515 A | 8/1995 | Khosravi et al. |
| 5,522,817 A | 6/1996 | Sander et al. |
| 5,525,706 A | 6/1996 | Gruber et al. |
| 5,527,337 A | 6/1996 | Stack et al. |
| 5,527,341 A | 6/1996 | Gogolewski et al. |
| 5,533,519 A | 7/1996 | Radke et al. |
| 5,584,836 A | 12/1996 | Ballintyn et al. |
| 5,630,835 A | 5/1997 | Brownlee |
| 5,633,002 A | 5/1997 | Stricker et al. |
| 5,634,936 A | 6/1997 | Linden et al. |
| 5,660,846 A | 8/1997 | Cheikh |
| 5,676,146 A | 10/1997 | Scarborough |
| 5,716,410 A | 2/1998 | Wang et al. |
| 5,716,413 A | 2/1998 | Walter et al. |
| 5,733,330 A | 3/1998 | Cox |
| 5,735,887 A | 4/1998 | Barreras, Sr. et al. |
| 5,760,118 A | 6/1998 | Sinclair et al. |
| 5,766,239 A | 6/1998 | Cox |
| 5,766,618 A | 6/1998 | Laurencin et al. |
| 5,792,400 A | 8/1998 | Talja et al. |
| 5,833,603 A | 11/1998 | Kovacs et al. |
| 5,836,989 A | 11/1998 | Shelton |
| 5,873,843 A | 2/1999 | Draper |
| 5,893,850 A | 4/1999 | Cachia |
| 5,904,658 A | 5/1999 | Niederauer et al. |
| 5,904,708 A | 5/1999 | Goedeke |
| 5,908,918 A | 6/1999 | Chen et al. |
| 5,935,172 A | 8/1999 | Ochoa et al. |
| 6,013,080 A | 1/2000 | Khalili |
| 6,022,352 A | 2/2000 | Vandewalle |
| 6,071,312 A | 6/2000 | Lampe et al. |
| 6,077,989 A | 6/2000 | Kandel et al. |
| 6,187,008 B1 | 2/2001 | Hamman |
| 6,203,573 B1 | 3/2001 | Walter et al. |
| 6,206,881 B1 | 3/2001 | Frigg et al. |
| 6,248,108 B1 | 6/2001 | Tormala et al. |
| 6,248,430 B1 | 6/2001 | Toyoda et al. |
| 6,281,262 B1 | 8/2001 | Shikinami |
| 6,344,496 B1 | 2/2002 | Niederauer et al. |
| 6,375,465 B1 | 4/2002 | Engman et al. |
| 6,423,062 B2 | 7/2002 | Enayati |
| 6,425,923 B1 | 7/2002 | Stalcup et al. |
| 6,436,136 B1 | 8/2002 | Flodin et al. |
| 6,503,278 B1 | 1/2003 | Pohjonen et al. |
| 6,511,511 B1 | 1/2003 | Slivka et al. |
| 6,514,286 B1 | 2/2003 | Leatherbury et al. |
| 6,565,606 B1 | 5/2003 | Bruce et al. |
| 6,605,090 B1 | 8/2003 | Trieu et al. |
| 6,675,044 B2 | 1/2004 | Chen |
| 6,719,935 B2 | 4/2004 | Tunc |
| 6,738,671 B2 | 5/2004 | Christophersom et al. |
| 6,764,446 B2 | 7/2004 | Wolinsky et al. |
| 6,766,200 B2 | 7/2004 | Cox |
| 6,783,712 B2 | 8/2004 | Slivka et al. |
| 6,790,372 B2 | 9/2004 | Roy et al. |
| 6,793,659 B2 | 9/2004 | Putnam |
| 6,819,247 B2 | 11/2004 | Birnbach et al. |
| 6,834,436 B2 | 12/2004 | Townsend et al. |
| 6,841,111 B2 | 1/2005 | Rickner et al. |
| 6,881,766 B2 | 4/2005 | Hain |
| 6,908,466 B1 | 6/2005 | Bonutti et al. |
| 6,916,321 B2 | 7/2005 | TenHuisen et al. |
| 6,926,670 B2 | 8/2005 | Rich et al. |
| 6,939,299 B1 | 9/2005 | Petersen et al. |
| 6,968,743 B2 | 11/2005 | Rich et al. |
| 7,005,543 B2 | 2/2006 | Zhang |
| 7,027,871 B2 | 4/2006 | Burnes et al. |
| 7,033,603 B2 | 4/2006 | Nelson et al. |
| 7,034,694 B2 | 4/2006 | Yamaguchi et al. |
| 7,090,676 B2 | 8/2006 | Huebner et al. |
| 7,097,662 B2 | 8/2006 | Evans, III et al. |
| 7,151,914 B2 | 12/2006 | Brewer |
| 7,209,790 B2 | 4/2007 | Thompson et al. |
| 7,212,133 B2 | 5/2007 | Goetz et al. |
| 7,261,716 B2 | 8/2007 | Strobel et al. |
| 7,261,734 B2 | 8/2007 | Gellman et al. |
| 7,333,013 B2 | 2/2008 | Berger |
| 7,381,223 B2 | 6/2008 | Kovacevic |
| 7,559,951 B2 | 7/2009 | DiSilvestro et al. |
| 7,729,758 B2 | 6/2010 | Haller et al. |
| 7,794,495 B2 | 9/2010 | Gale et al. |
| 8,007,450 B2 | 8/2011 | Williams |
| 8,267,990 B2 | 9/2012 | Gale et al. |
| 8,394,488 B2 | 3/2013 | Davé et al. |
| 8,722,783 B2 | 5/2014 | Rose et al. |
| 8,828,419 B2 | 9/2014 | Davé et al. |
| 8,870,945 B2 | 10/2014 | Dave et al. |
| 9,000,066 B2 | 4/2015 | Brown et al. |
| 9,120,919 B2 | 9/2015 | Brown |
| 9,308,293 B2 | 4/2016 | Brown et al. |
| 2001/0021873 A1 | 9/2001 | Stinson |
| 2001/0034528 A1 | 10/2001 | Foerster et al. |
| 2002/0022588 A1 | 2/2002 | Wilkie et al. |
| 2002/0029041 A1 | 3/2002 | Hover et al. |

(56) References Cited

U.S. PATENT DOCUMENTS

| | | |
|---|---|---|
| 2002/0029043 A1 | 3/2002 | Ahrens et al. |
| 2002/0082683 A1 | 6/2002 | Stinson et al. |
| 2002/0082685 A1* | 6/2002 | Sirhan .................. A61F 2/90 623/1.42 |
| 2003/0045941 A1 | 3/2003 | Lewallen |
| 2003/0114937 A1 | 6/2003 | Leatherbury et al. |
| 2003/0125745 A1 | 7/2003 | Tseng et al. |
| 2003/0139812 A1 | 7/2003 | Garcia et al. |
| 2004/0010313 A1* | 1/2004 | Aston .................. A61L 31/146 623/17.11 |
| 2004/0019356 A1 | 1/2004 | Fraser et al. |
| 2004/0019386 A1 | 1/2004 | Ferree |
| 2004/0030379 A1* | 2/2004 | Hamm .................. A61K 31/335 623/1.15 |
| 2004/0059336 A1 | 3/2004 | Lombardo et al. |
| 2004/0077073 A1 | 4/2004 | Schindler et al. |
| 2004/0092818 A1 | 5/2004 | Weaver et al. |
| 2004/0106734 A1 | 6/2004 | Rose |
| 2004/0116837 A1 | 6/2004 | Yamaguchi et al. |
| 2004/0152972 A1 | 8/2004 | Hunter |
| 2004/0156878 A1 | 8/2004 | Rezania et al. |
| 2004/0176815 A1 | 9/2004 | Janzig et al. |
| 2004/0204647 A1 | 10/2004 | Grupp et al. |
| 2004/0220668 A1 | 11/2004 | Eisermann et al. |
| 2004/0242722 A1 | 12/2004 | Rose et al. |
| 2004/0243129 A1 | 12/2004 | Moumene et al. |
| 2005/0008672 A1 | 1/2005 | Winterbottom et al. |
| 2005/0010139 A1 | 1/2005 | Aminian et al. |
| 2005/0013793 A1 | 1/2005 | Beckman et al. |
| 2005/0021029 A1 | 1/2005 | Trieu et al. |
| 2005/0055027 A1 | 3/2005 | Yeung et al. |
| 2005/0085313 A1 | 4/2005 | Nishitani |
| 2005/0085812 A1 | 4/2005 | Sherman et al. |
| 2005/0099290 A1 | 5/2005 | Govari |
| 2005/0101833 A1 | 5/2005 | Hsu et al. |
| 2005/0107886 A1 | 5/2005 | Crabtree et al. |
| 2005/0131397 A1 | 6/2005 | Levin |
| 2005/0159812 A1 | 7/2005 | Dinger, III et al. |
| 2005/0165128 A1 | 7/2005 | Cohn et al. |
| 2005/0177245 A1 | 8/2005 | Leatherbury et al. |
| 2005/0187555 A1 | 8/2005 | Biedermann et al. |
| 2005/0234555 A1 | 10/2005 | Sutton et al. |
| 2005/0247319 A1 | 11/2005 | Berger |
| 2005/0273106 A1 | 12/2005 | Von Oepen |
| 2005/0288727 A1 | 12/2005 | Penner |
| 2006/0009656 A1 | 1/2006 | Zhang |
| 2006/0047283 A1 | 3/2006 | Evans, III et al. |
| 2006/0052782 A1 | 3/2006 | Morgan et al. |
| 2006/0058627 A1 | 3/2006 | Flaherty et al. |
| 2006/0067973 A1 | 3/2006 | Schachter |
| 2006/0069447 A1 | 3/2006 | DiSilvestro et al. |
| 2006/0079900 A1 | 4/2006 | Mathieu et al. |
| 2006/0111291 A1 | 5/2006 | DiMauro et al. |
| 2006/0129050 A1 | 6/2006 | Martinson et al. |
| 2006/0136071 A1 | 6/2006 | Maspero et al. |
| 2006/0161159 A1 | 7/2006 | Dreyfuss et al. |
| 2006/0178748 A1 | 8/2006 | Dinger, III et al. |
| 2006/0188547 A1 | 8/2006 | S. Bezwada |
| 2006/0190080 A1 | 8/2006 | Danoff et al. |
| 2006/0200031 A1 | 9/2006 | White et al. |
| 2006/0235410 A1 | 10/2006 | Ralph et al. |
| 2006/0271112 A1 | 11/2006 | Martinson et al. |
| 2006/0271199 A1 | 11/2006 | Johnson |
| 2007/0041950 A1 | 2/2007 | Leatherbury et al. |
| 2007/0043376 A1 | 2/2007 | Leatherbury et al. |
| 2007/0078497 A1 | 4/2007 | Vandanacker |
| 2007/0089518 A1 | 4/2007 | Ericson et al. |
| 2007/0123938 A1 | 5/2007 | Haller et al. |
| 2007/0128154 A1 | 6/2007 | Hadba et al. |
| 2007/0129769 A1 | 6/2007 | Bourget et al. |
| 2007/0134305 A1 | 6/2007 | Zilberman |
| 2007/0185488 A1 | 8/2007 | Pohjonen et al. |
| 2007/0191963 A1 | 8/2007 | Winterbottom et al. |
| 2007/0219639 A1 | 9/2007 | Otto et al. |
| 2007/0270691 A1 | 11/2007 | Bailey et al. |
| 2007/0270833 A1 | 11/2007 | Bonutti et al. |
| 2007/0276383 A1 | 11/2007 | Rayhack |
| 2008/0045627 A1 | 2/2008 | Rose |
| 2008/0085297 A1 | 4/2008 | Dave et al. |
| 2008/0086199 A1 | 4/2008 | Dave et al. |
| 2008/0154310 A1 | 6/2008 | White et al. |
| 2008/0177291 A1 | 7/2008 | Jensen et al. |
| 2008/0183221 A1 | 7/2008 | Burdilis |
| 2008/0300597 A1 | 12/2008 | Morgan et al. |
| 2010/0016985 A1 | 1/2010 | Rabiei |
| 2010/0069547 A1 | 3/2010 | Brown et al. |
| 2010/0137491 A1 | 6/2010 | Rose et al. |
| 2010/0152621 A1 | 6/2010 | Janna et al. |
| 2011/0098803 A1 | 4/2011 | Gale et al. |

FOREIGN PATENT DOCUMENTS

| | | |
|---|---|---|
| EP | 1099415 | 5/2001 |
| EP | 1541095 | 6/2005 |
| EP | 1642550 | 4/2006 |
| EP | 1660146 | 5/2006 |
| EP | 1704893 | 9/2006 |
| GB | 2330078 | 4/1999 |
| WO | WO9609014 | 3/1996 |
| WO | WO9626678 | 9/1996 |
| WO | WO9629007 | 9/1996 |
| WO | WO9720512 | 6/1997 |
| WO | WO0018317 | 4/2000 |
| WO | WO0019888 | 4/2000 |
| WO | WO0030534 | 6/2000 |
| WO | WO0119248 | 6/2001 |
| WO | WO02058551 | 10/2002 |
| WO | WO02056763 | 11/2002 |
| WO | WO03008570 | 1/2003 |
| WO | WO2004052453 | 6/2004 |
| WO | WO2004052456 | 6/2004 |
| WO | WO2005018684 | 3/2005 |
| WO | WO2005018698 | 3/2005 |
| WO | WO2005084544 | 9/2005 |
| WO | WO2005104997 | 11/2005 |
| WO | WO2005120203 | 12/2005 |
| WO | WO2006045607 | 5/2006 |
| WO | WO2006055547 | 5/2006 |
| WO | WO2006089069 | 8/2006 |
| WO | WO2006094273 | 9/2006 |
| WO | WO2006131302 | 12/2006 |
| WO | WO2007009088 | 1/2007 |
| WO | WO2007009123 | 1/2007 |
| WO | WO2007025191 | 3/2007 |
| WO | WO2007061890 | 5/2007 |
| WO | WO2007069251 | 6/2007 |
| WO | WO2007086832 | 8/2007 |
| WO | WO2007138062 | 12/2007 |
| WO | WO2008022136 | 2/2008 |
| WO | WO2008044011 | 4/2008 |
| WO | WO2010004261 | 1/2010 |
| WO | WO2010045473 | 4/2010 |
| WO | WO2011082152 | 7/2011 |
| WO | WO2013012731 | 1/2013 |

OTHER PUBLICATIONS

International Search Report for International Application No. PCT/US2006/033326, dated Dec. 13, 2006.

International Preliminary Report on Patentability for International Application No. PCT/US2006/033326, dated Feb. 28, 2008.

Kishida, A., et al., "Formulation-Assisted Biodegradable Polymer Matrices," Communications to the Editor, Chem. Pharm. Bull. 37(7) 1954-1956 (1989).

Oyama, H.T., et al., "Rapid controlled hydrolytic degradation of poly(L-lactic acid) by blending with poly(aspartic acid-co-L-lactide)," Polymer Degradation and Stability, 94 (2009) 1419-1426.

* cited by examiner

SYSTEMS AND METHODS FOR DELIVERING A MEDICAMENT

CROSS REFERENCE TO RELATED APPLICATIONS

The present application is a National Stage of International Application No. PCT/US2007/005533, filed Mar. 2, 2007, which claims priority to U.S. provisional patent application No. 60/778,778, entitled "Apparatus and Method for Dispensing a Medicament," filed Mar. 3, 2006. The entire contents of each prior application are incorporated herein by reference.

FIELD OF THE INVENTION

The present invention relates generally to systems and methods for delivering a medicament that is associated with an implant.

BACKGROUND OF THE INVENTION

Implants, such as orthopaedic implants or stents, in a patient may become infected after implantation. For example, infectious cells, such as bacteria cells, may form around the implant or attach to the implant. In addition, infectious cells may form a layer of material or biofilm over themselves to protect the infectious cells from medicaments, such as antibiotics, meant to kill or disrupt the infectious cells. To treat the infected area, health-care providers often remove the implant, apply a medicament, such as an antibiotic, to the infected area, and re-implant the implant.

Health-care providers can supplement removing the implant by introducing a medicament systemically, such as providing the patient with a medicament in pill form that the patient orally ingests, or by injecting a medicament directly into, or in proximity to, the infected area. In some instances, a medicament is attached to the implant and released when exposed to body tissue after re-implantation.

Such treatment procedures are sometimes unsuccessful due to complications or infections that return at a later time. Additional infections may also occur when the health-care provider removes and re-implants the implant. Physiologic phenomenon, such as infectious cells forming a biofilm that protects the cells from a medicament released just after implantation, may prevent or inhibit a medicament delivered by such treatment procedures from effectively treating the infection. Furthermore, a medicament delivery system that releases a medicament at the same time, or shortly after, implantation may not effectively treat the infected area or infectious cells that develop at a period of time after implantation.

Accordingly, a need exists for a medicament delivery system and method that can release a medicament at a time selected by a health-care professional. A need further exists for a medicament delivery method that can release a medicament at a selected time without requiring the removal of an implant. A need further exists for a medicament delivery system and method that provides for delivery a medicament at a customizable time and/or rate selected by a health-care professional.

SUMMARY OF THE INVENTION

Aspects and embodiments of the present invention provide methods and systems for delivering a medicament at a level selected by an energy source user, such as a health-care professional. In one embodiment of the present invention, a medicament containment device containing a medicament, such as for example an antibiotic, is attached to an implant that may be an orthopaedic implant or stent. The medicament containment device can degrade upon exposure to energy, such as energy from an energy source. The implant, including the medicament containment device, is implanted or inserted into an environment such as a patient's body. An energy source can be used outside the patient's body, but in proximity to the implant, to apply energy to the medicament containment device. Upon exposure to the energy, the medicament containment device can disintegrate, degrade, or otherwise alter in structure or composition or both, partially or totally, sufficient to allow a medicament to penetrate (hereinafter "degrade") and release at least part of the medicament into the environment. The medicament can kill and/or disrupt bacterial cells or other infectious cells that form in proximity to the implant.

In some embodiments of the present invention, the medicament containment device may include at least a first layer and a second layer. The first layer can substantially surround the second layer. The second layer can substantially surround a medicament. The first layer can degrade upon exposure to energy from an energy source and expose the second layer to the environment. The second layer can be a resorbable layer that, when exposed to the environment, degrades over time and substantially releases the medicament.

In some embodiments of the present invention, an energy source is provided that is adapted to apply energy to bacteria cells attached to or around an implant and kill or disrupt the bacteria cells. The energy may also disrupt a bacteria film to allow a medicament delivered using any desired method to kill the bacteria cells.

According to an aspect of the present invention, there may be provided a medicament containment device for association with an implant, the medicament containment device comprising a medicament, a first layer substantially surrounding a second layer, the second layer substantially surrounding the medicament, wherein the first layer is adapted to at least partially degrade when the first layer is exposed to energy from an energy source, and wherein the second layer is adapted to at least partially degrade and release at least part of the medicament after the first layer degrades.

According to one embodiment of the present invention, the first layer at least partially exposes the second layer to an environment and the second layer is a resorbable layer and is adapted to at least partially degrade after exposure to the environment.

According to one embodiment of the present invention, the medicament containment device further comprises a first medicament between the first layer and the second layer, wherein the medicament substantially surrounded by the second layer is a second medicament.

According to one embodiment of the present invention, the first layer is adapted to degrade at a first resonant frequency and the second layer is adapted to degrade at a second resonant frequency.

According to one embodiment of the present invention, the implant is a resorbable implant adapted to degrade over a period of time and the medicament is a resorbtion acceleration agent and the resorbtion acceleration agent is adapted to increase the rate of degradation by the resorbable implant.

According to one embodiment of the present invention, the energy is at least one of an ultrasound wave, thermal, light wave, radar, sonar, ultraviolet light wave, microwave, electrical, magnetic field, vibratory, and laser.

According to one embodiment of the present invention, the implant is an orthopaedic implant.

According to an aspect of the present invention, a method is provided for delivering a medicament from a medicament containment device, the medicament containment device having at least one layer containing the medicament, the method comprising associating the medicament containment device with an implant, the implant being implanted into a patient body, applying energy to the medicament containment device, at least partially degrading the at least one containment device layer with the applied energy, and releasing the medicament from the medicament containment device after the at least one layer at least partially degrades.

According to one embodiment of the present invention, the method further comprises providing the medicament containment device having a first layer and a second layer, the first layer substantially surrounding the second layer and the second layer substantially surrounding the medicament.

According to one embodiment of the present invention, the method further comprises at least partially degrading the first layer with the applied energy, at least partially degrading the second layer, and releasing the medicament from the medicament containment device after the second layer at least partially degrades.

According to one embodiment of the present invention, the method further comprises exposing the second layer to an environment after the first layer at least partially degrades and the second layer at least partially degrades after exposure to the environment.

According to one embodiment of the present invention, associating the medicament containment device with the implant comprises attaching the medicament containment device to the implant.

According to one embodiment of the present invention, attaching the medicament containment device to the implant comprises providing a pool comprising a plurality of medicament containment devices, applying an adhesive paste to the implant, and dipping the implant having adhesive paste into the pool.

According to one embodiment of the present invention, the method further comprises associating the medicament containment device with the implant comprises inserting the medicament containment device in proximity to the implant in a patient body.

According to one embodiment of the present invention, the at least one layer is a seal.

According to one embodiment of the present invention, the implant is an orthopaedic implant.

According to an aspect of the present invention, a system is provided comprising an energy source adapted to release energy, an implant in a patient body comprising a medicament containment device, the medicament containment device comprising a at least one layer comprising a medicament, wherein the energy is adapted to at least partially degrade the at least one layer, and wherein the medicament containment device is adapted to release at least part of the medicament after the at least one layer at least partially degrades.

According to one embodiment of the present invention, the energy source is located inside the patient body.

According to one embodiment of the present invention, the energy source is located outside the patient body.

According to one embodiment of the present invention, the medicament containment device comprises a well reservoir adapted to store the medicament, a seal, and wherein the seal is adapted to at least partially degrade after exposure to the energy.

According to one embodiment of the present invention, the energy is adapted to disrupt bacteria colonies around the orthopaedic implant.

According to one embodiment of the present invention, the medicament containment device comprises a first layer substantially surrounding a second layer, the second layer substantially surrounding the medicament, wherein the first layer is adapted to at least partially degrade when the first layer is exposed to energy from an energy source, and wherein the second layer is adapted to at least partially degrade and release at least part of the medicament after the first layer degrades.

According to one embodiment of the present invention, the system further comprises a first medicament between the first layer and the second layer, wherein the medicament substantially surrounded by the second layer is a second medicament.

According to one embodiment of the present invention, the first layer is adapted to degrade at a first resonant frequency and the second layer is adapted to degrade at a second resonant frequency.

According to one embodiment of the present invention, the energy source is adapted to release energy at the first resonant frequency and the second resonant frequency.

According to one embodiment of the present invention, the second layer is a resorbable layer that is adapted to at least partially degrade after exposure to body tissue.

According to one embodiment of the present invention, the implant is an orthopaedic implant.

'Embodiment' as used herein can be considered to mean an aspect or object of the invention, and vice versa.

BRIEF DESCRIPTION OF THE DRAWINGS

These and other features, aspects, and advantages of the present invention are better understood when the following Detailed Description of the Invention is read with reference to the accompanying drawings, wherein.

DETAILED DESCRIPTION OF THE INVENTION

Figure 1:
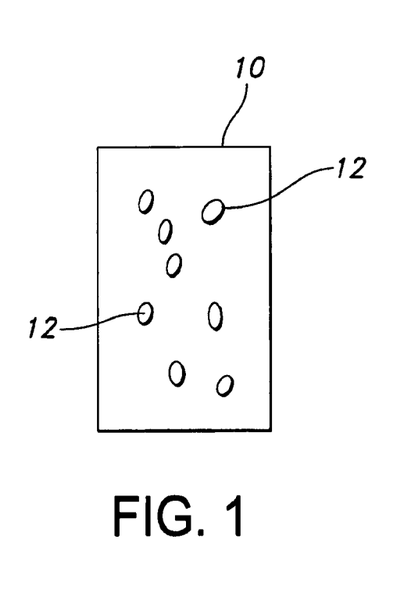
FIG. 1 illustrates an environment including medicament containment devices according to one embodiment of the present invention.

Certain aspects and embodiments of the present invention provide a medicament delivery system and method that allows a medicament to be delivered to an environment, such as a patient's internal body, at a selected time after implantation of an implant into a patient's body. FIG. 1 shows an environment 10 containing a plurality of medicament containment devices 12. The environment 10 may be inside the patient's body after implantation of an implant (not shown). The containment devices 12 may be attached, embedded in, or otherwise associated with the implant and include a layer surrounding a medicament within the containment device 12. 'Medicament' as used herein may include any medicine or other composition which can be used to promote healing or recovering, such as from an infection (whether bacterial, viral, or otherwise). Examples of suitable medicament for use in connection with various embodiments of the present invention includes osteoblast affecting agents, osteoclast affecting agents, antibiotics, anti-inflammatory agents, pain medication, osteogenic factors, prostaglandins, radio-markers, angiogenic factors, vasodilators, growth factors, or a combination of any of the above.

Figure 2:
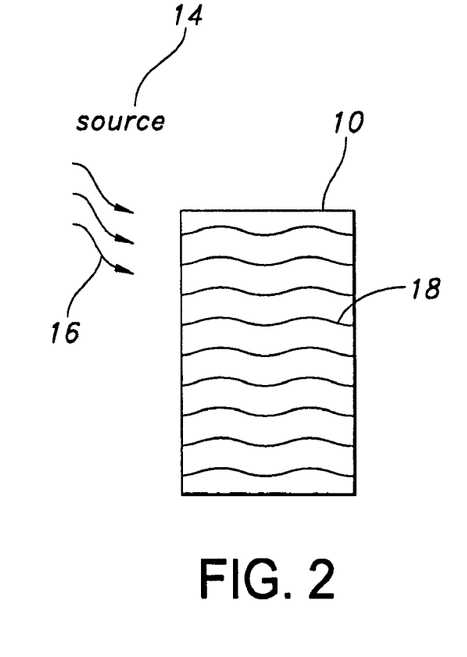
FIG. 2 illustrates the environment of FIG. 1 with the medicament substantially released from the medicament containment devices.

The layer may be adapted to degrade or otherwise substantially release the medicament upon exposure to energy from an energy source. For example, FIG. 2 shows an energy source as source 14 releasing energy 16 that degrades the layer of containment devices 12. The medicament 18 is then substantially released into the environment 10. The containment devices 12 may be adapted to release the medicament 18 in one stage, such as all at one time, or more than one stage over a period of time.

In some embodiments of the present invention, the layer degrades after exposure to energy at a resonant frequency. The energy source 14 may release energy 16 at the resonant frequency of the layer. One example of the energy 16 is an ultrasound signal at the resonant frequency of the layer. Other types of energy 16 may include thermal, light waves, radar, sonar, ultraviolet light waves, microwaves, electricity, magnetic fields, vibratory, and laser.

The energy source 14 may be outside or inside the patient's body. In one embodiment, the energy source 14 is a separate device outside the body that may, for example, allow a user to controllably release energy 16.

In another embodiment, the energy source 14 can be inserted and maintained within the patient's body. The energy source 14 could be self-sufficient within the patient's body, such that it requires no communication with or link to any device outside of the patient's body to apply energy 16 to the containment devices 12. The energy source 14 may also be attached, embedded or otherwise associated with the implant or another device inserted into the patient's body. In another embodiment, the energy source 14 can communicate with another device outside the patient's body through a wire or wirelessly. The device outside the patient's body could be used to control the energy source 14, such as when to apply energy 16 and the characteristics of the applied energy 16.

The energy source 14 may communicate with a separate device that channels, carries, and/or amplifies the applied energy 16. For example, energy 16 that is vibration energy can be carried by a material, such as a vibrating beam having a geometry adapted to direct or focus the energy 16 to the desired area. However, a carrier or amplification device may be used for any type of energy 16.

The containment device layer may include a first layer and a second layer. As described in more detail below, the first layer may be an outer layer that degrades upon exposure to the energy 16 and exposes the second layer to the environment 10. The second layer may be an inner layer that is resorbable, absorbable, or otherwise adapted to degrade over a period of time after exposure to the environment 10 to substantially release the medicament 18. The second layer may also have the same or different resonant frequency than the first layer. For example, the second layer may degrade upon exposure to energy at a different frequency than the energy 16 to substantially release the medicament. In other embodiments, the second layer has no resonant frequency.

In some embodiments, the first layer may substantially surround a first medicament layer, the second layer, and a second medicament layer. The second layer may substantially surround the second medicament layer. Upon exposure to the energy 16, the first layer can degrade and substantially release the first medicament layer. The second layer may then be exposed to an energy at the same or different frequency and degrade to substantially release the second medicament layer. The medicament layers may be different volumes to provide a health-care professional with additional options to deliver the desired amount and type of medicament.

Furthermore, the layer of each of the containment devices 12 may have different resonant frequencies. Each containment device 12 may release medicament at different resonant frequencies and allow a health-care professional to select when and how much medicament to release.

Figure 3:
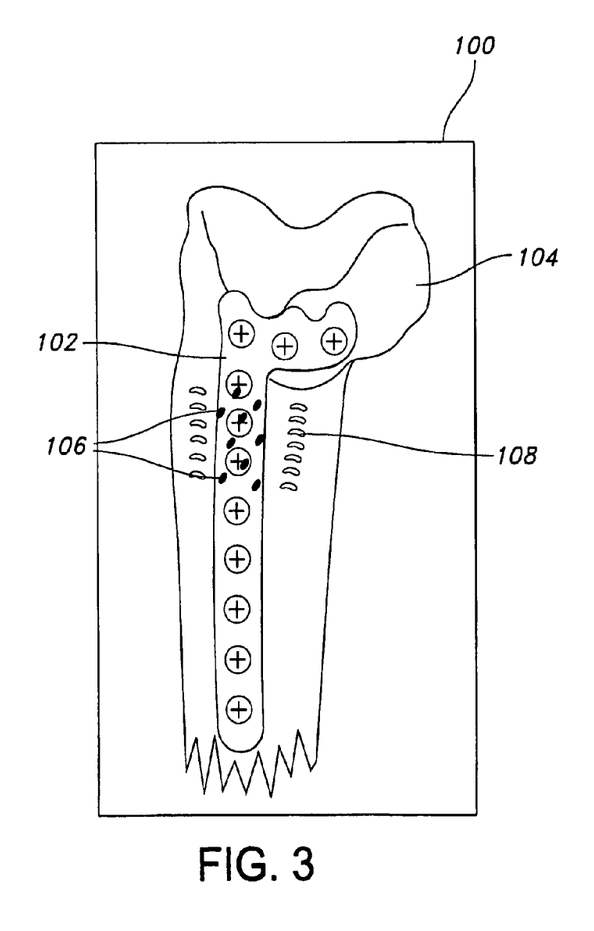
FIG. 3 illustrates medicament containment devices attached to an orthopaedic implant according to one embodiment of the present invention.
Figure 4:
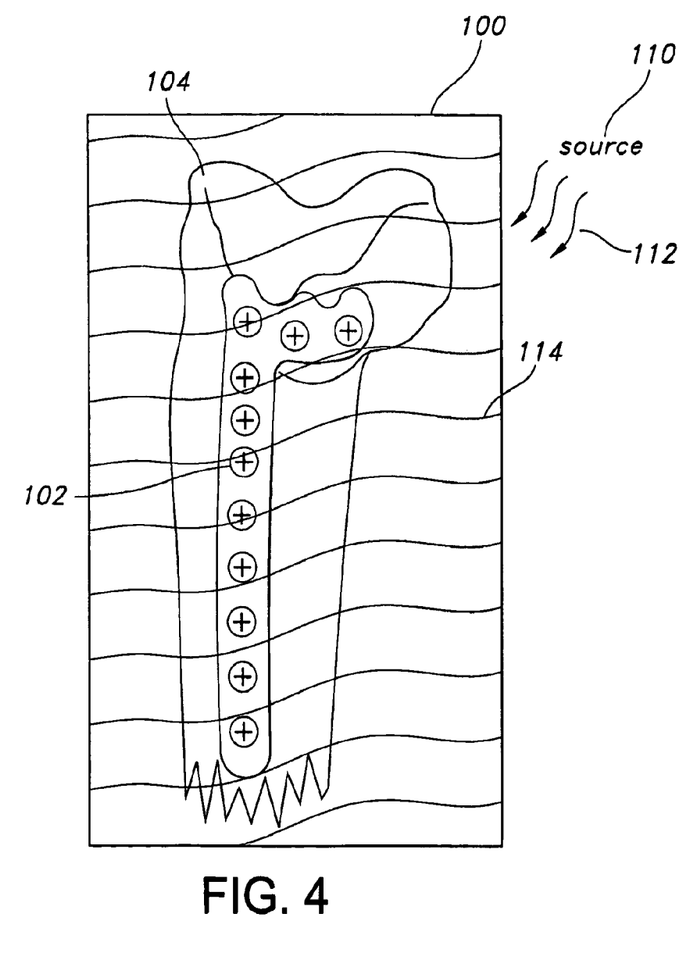
FIG. 4 illustrates the orthopaedic implant of FIG. 3 with the medicament substantially released from the medicament containment devices.

As stated above, medicament containment devices according to some embodiments of the present invention may be attached, embedded, or otherwise associated with an implant. FIGS. 3-4 illustrate a environment 100 including an implant, such as orthopaedic implant 102, associated with a bone 104. The orthopaedic implant 102 may be any type of orthopaedic implant such as an internal fixation device, examples of which include an intermedullary plate and nail. A plurality of containment devices 106 are associated with the orthopaedic implant 102 prior to implantation. For example, the orthopaedic implant 102 may be covered with an adhesive paste and containment devices 106 are attached to the orthopaedic implant 102 using the adhesive paste. Alternatively or additionally, indentions may be created in the orthopaedic implant 102 and containment devices 106 can be embedded or attached in the indentions.

A bacteria colony 108 may form around the orthopaedic implant 102 after implantation as result of an infection. An energy source 110 that is located outside of the patient's body can be used to apply energy 112 to the containment devices 106 and substantially release medicament 114 to kill or otherwise disrupt the bacteria colony 108.

In some embodiments, the orthopaedic implant 102 may be a resorbable orthopaedic implant adapted to degrade after a period of time, such as after the orthopaedic implant is no longer needed to heal or otherwise treat a patient's injury. The containment devices 106 may contain a medicament that is a resorbtion acceleration agent adapted to increase the rate at which the orthopaedic implant 102 degrades. The energy source 110 may be used to apply energy 112 to the containment devices 106. Upon exposure to the energy 112, the containment devices 106 may degrade and substantially release the resorbtion acceleration agent to the environment 100. The resorbtion acceleration agent can interact with the resorbable orthopaedic implant and increase the rate at which the orthopaedic implant 102 degrades.

Figures 5, 6, 7:
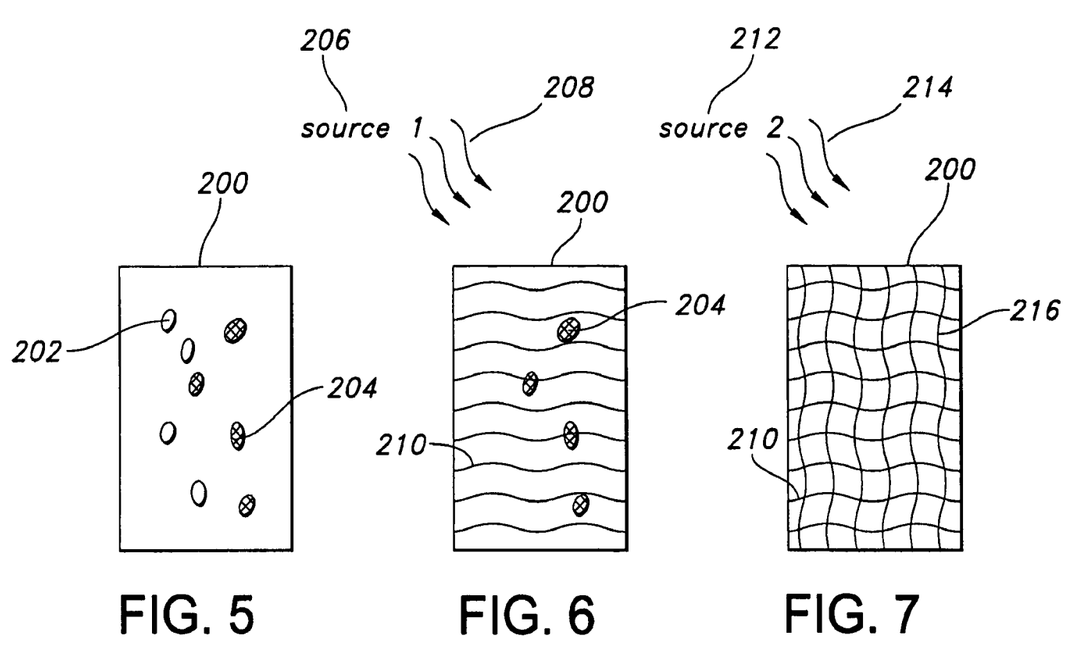
FIG. 5 illustrates an environment including two types of medicament containment devices according to one embodiment of the present invention.
FIG. 6 illustrates medicament substantially released from the first type of medicament containment devices of FIG. 5.
FIG. 7 illustrates medicament substantially released from the second type of medicament containment devices of FIG. 5.

FIG. 5 shows an environment 200 including two types of medicament containment devices; first medicament containment devices 202 and second medicament containment devices 204. Each of the containment devices 202, 204 substantially surrounds a medicament and can be associated with an implant. The medicament in the first containment devices 202 may be the same or different than the second containment devices 204. The first containment devices 202 and second containment devices 204 may degrade after exposure to different types of energy providing a health-care professional with additional options in selecting the rate and type of medicament to release after implantation.

A first energy source 206, shown in FIG. 6, may be used to apply a first type of energy 208. The first containment devices 202 may have characteristics that are affected by first type of energy, such as degrading after exposure to the first type of energy 208 and releasing medicament 210 into the environment 200. The second containment devices 204 can have characteristics such that they do not degrade after exposure to the first type of energy 208 and remain intact. For example, the first energy source 206 may release energy 208 at a frequency different from the resonant frequency of the second containment devices 204.

A second energy source 212, shown in FIG. 7, may be used to apply a second type of energy 214. The second containment devices 204 may have characteristics that cause it to degrade after exposure to the second type of energy 214 and substantially release medicament 216 into the environment 200.

The first energy source 206 and second energy source 210 may be the same device adapted to release energy with at least two different characteristics. For example, energy 208 and energy 214 may be an ultrasound signal released at different frequencies. A user may use the second energy source 212 to release the second type of energy 214 at the same time or at a different time than the first type of energy 208.

Furthermore, any number of containment devices may be included in the environment 200 and each may substantially release medicament after exposure to energy with different characteristics. A user can select the amount and time for releasing the medicament based on the energy characteristics he or she applies to the containment devices. For example, the volume of released medicament may be controlled by the user by applying energy with selected characteristics at different times.

Figures 8, 9:
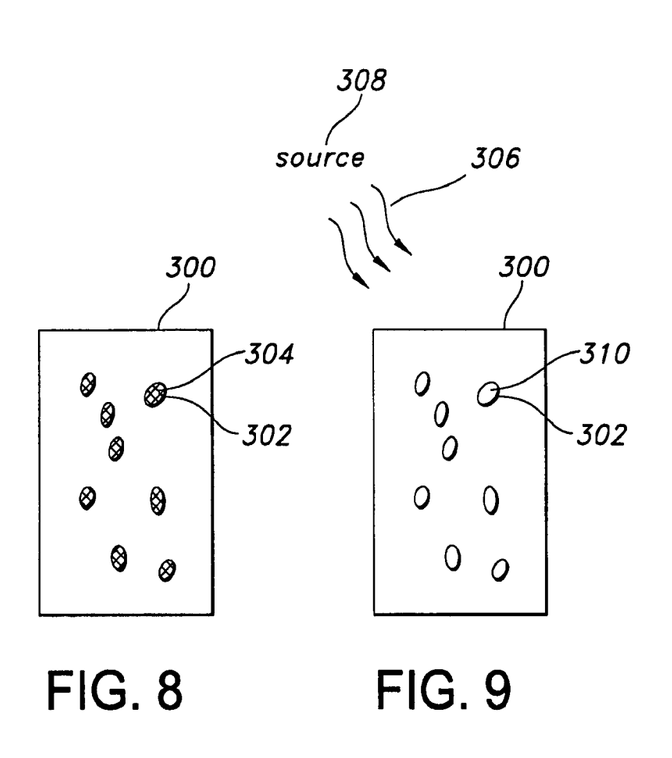
FIG. 8 illustrates an environment including medicament containment devices with a resorbable layer according to one embodiment of the present invention.
FIG. 9 illustrates the medicament containment devices of FIG. 8 with the resorbable layer removed.
Figure 10:
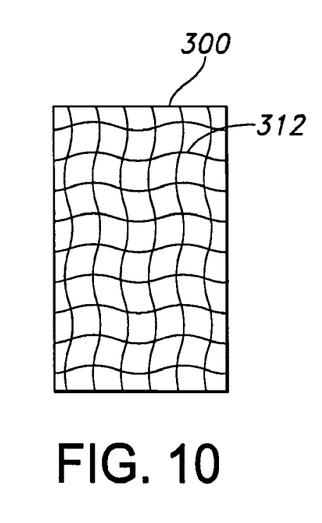
FIG. 10 illustrates medicament substantially released from the medicament containment devices of FIG. 9.

FIGS. 8-10 show an environment 300 including time release medicament containment devices 302. The environment 300 may be inside a patient's body. The containment devices 302 may include two layers. A first layer 304 can be adapted to degrade after exposure to energy 306 from an energy source 308 to expose a second layer 310.

The second layer 310 of each containment device 302 substantially surrounds a medicament and can be a resorbable, absorbable, or other type of layer that can degrade over time after exposure to the environment 300. The second layer 310 may be adapted to incrementally degrade and substantially release the medicament 312 over a period of time.

Figures 11, 12:
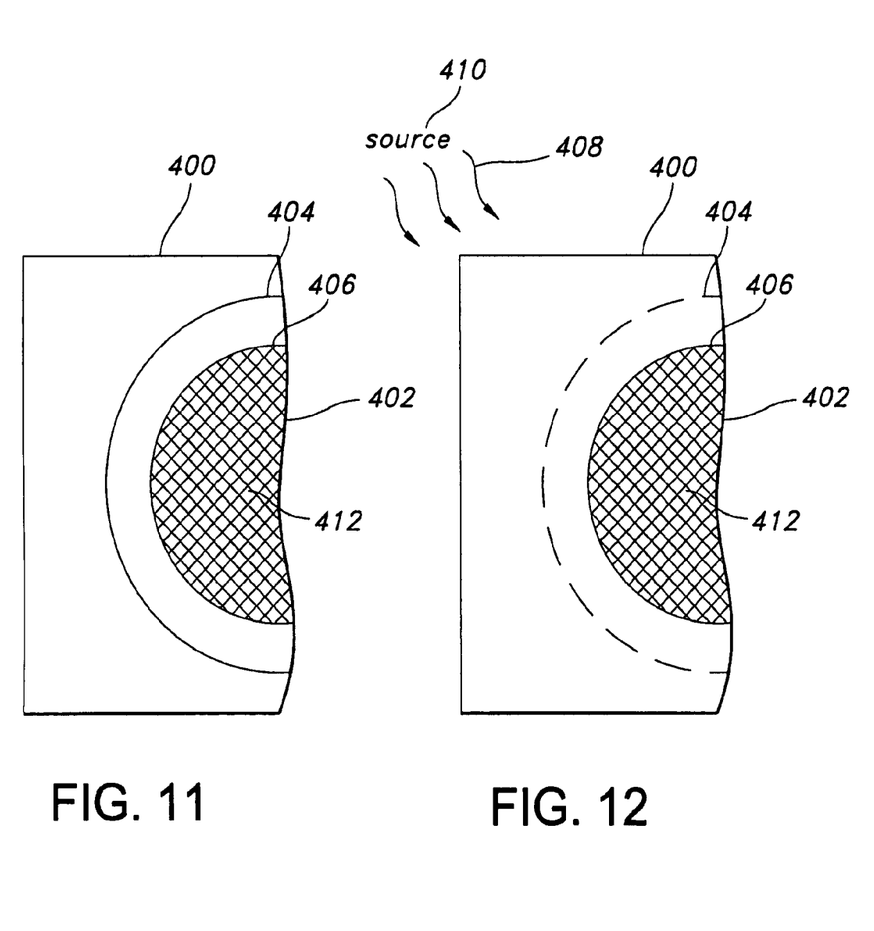
FIG. 11 illustrates a cross-sectional view of a medicament containment device according to one embodiment of the present invention.
FIG. 12 illustrates the medicament containment device of FIG. 11 with a first layer degrading.
Figure 13:
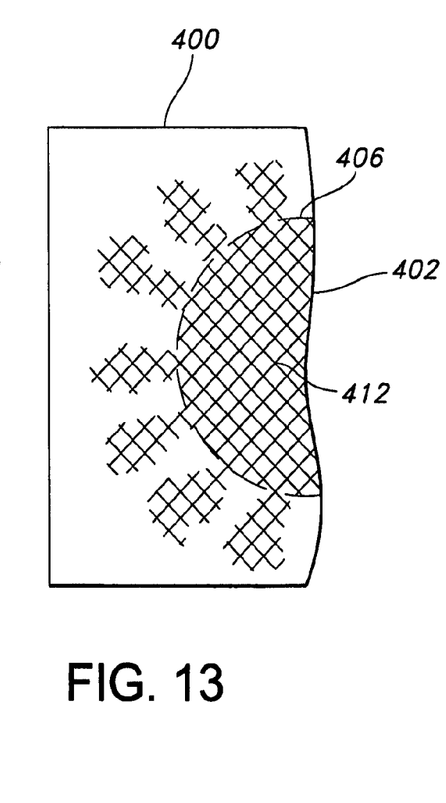
FIG. 13 illustrates the medicament containment device of FIG. 11 with a second layer degrading.

An example of a medicament containment device 402 with two layers 404, 406 is shown FIGS. 11-13. The containment device 402 is shown in an environment 400, such as inside a patient's body. The containment device 402 includes a first layer 404 and a second layer 406. The first layer 404 substantially surrounds the second layer 406 and can degrade after exposure to energy 408 from an energy source 410. After the first layer 404 at least partially degrades it can expose the second layer 406 to the environment 400. The second layer 406 substantially surrounds a medicament 412 and may be a resorbable, absorbable, or other type of layer that degrades over time after exposure to the environment 400 to substantially release a medicament 412.

An additional medicament layer may be included between the first layer 404 and second layer 406. When the first layer 404 is exposed to energy 408 and degrades, the additional medicament layer can be substantially released into the environment 400 to kill and/or disrupt bacteria colonies. The second layer 406 may be a resorbable, absorbable, or other type of layer that degrades over a period of time after the additional medicament layer is substantially released. The medicament 412 is then substantially released after the second layer 406 at least partially degrades.

In some embodiments, the second layer 406 may degrade after exposure to energy having different characteristics than the energy 408 used to degrade the first layer 404. For example, energy 408 is applied to the containment device 402 and the first layer 404 degrades, exposing the second layer 406 to the environment 400. At the same or later time, a second type of energy from the same or different energy source may be applied to the containment device 402. The second layer 406 may be made with characteristics to degrade after exposure to the second type of energy and not the energy 408.

Figure 14:
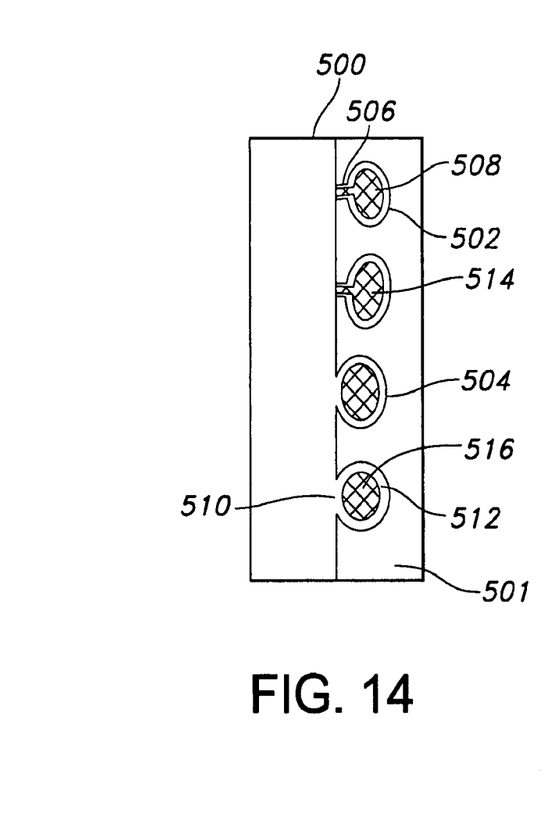
FIG. 14 illustrates an environment including an implant with medicament containment devices according to one embodiment of the present invention.
Figure 15:
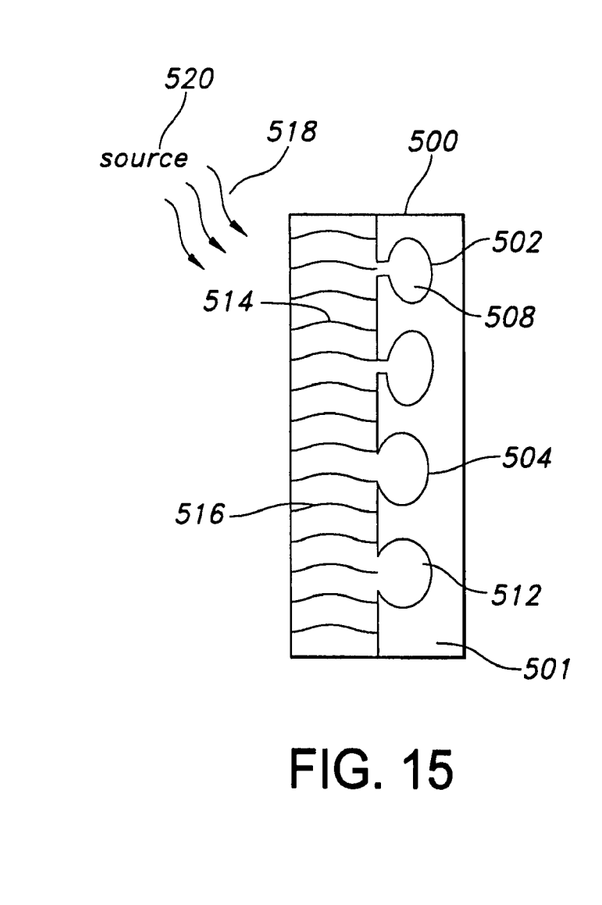
FIG. 15 illustrates medicament substantially released from the medicament containment devices of FIG. 14.

Medicament containment devices according to some embodiments of the present invention may be wells attached, embedded, or otherwise associated with an implant. FIGS. 14-15 show an environment 500 with an implant 501 containing medicament containment devices, such as wells 502, 504. The wells 502, 504 may be different configurations and include different environment access channels. For example, wells 502 may include an access channel such as tubes 506 between a well reservoir 508 and the environment 500. A seal may separate the environment 500 from the tubes 506. Wells 504 may include an access channel such as fenestrations 510 between a well reservoir 512 and the environment 500. A seal be located in the fenestrations 510 to separate the environment 500 from the well reservoir 512.

The well reservoirs 508, 512 can contain medicaments 514, 516 adapted to kill or otherwise disrupt a bacteria colony upon release into the environment. Energy 518 from an energy source 520 may be applied to the environment 500. The seals may break apart and substantially release the medicaments 514, 516 into the environment upon exposure to the energy 518. In some embodiments, the energy 518 breaks apart the seals and pumps the medicaments 514, 516 out of the well reservoirs 508, 512. For example, the energy 518 may be thermal energy that heats the medicaments 514, 516 to a level such that they exit the well reservoirs 508, 512 and into the environment 500. Alternatively, natural physical strain on the implant 501 can force medicament out of the well reservoirs 508, 512 after the seals are broken. Each of the seals may be configured to break apart after exposure to energy with different characteristics, such as for example different frequencies.

Figure 16:
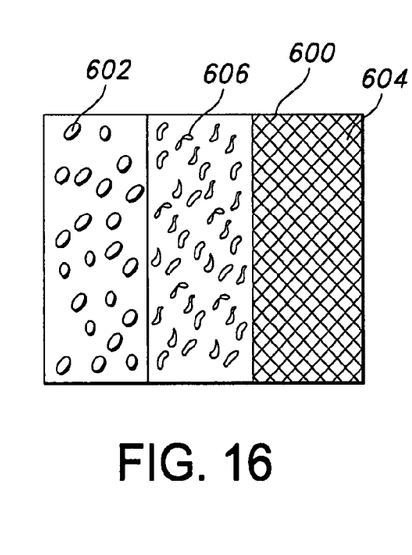
FIG. 16 illustrates an environment including medicament containment devices and bacteria colonies according to one embodiment of the present invention.

Medicament containment devices according to some embodiments of the present invention are not attached to or embedded with implants. FIG. 16 shows one embodiment of an environment 600 including an implant 604 and detached medicament containment devices 602. Although the medicament containment devices 602 are detached they are generally associated with the implant 604 by being located in relative proximity to the implant 604 in the environment 600. For example, the containment devices 602 are located in the general area of the implant 604 in a patient's body. In one embodiment, the containment devices 602 are located in the patient's body within 0.5 meters away from the implant 604.

The containment devices 602 can contain medicaments that can kill or disrupt infectious cells, such as bacteria colony 606. The bacteria colony 606 may form around the implant 604 and/or attach to the implant 604. The bacteria colony 606 may include bacteria cells and a biofilm forming a barrier between the bacteria cells and the environment 600. The medicament containment devices 602 may be injected into the environment after or at the same time of implantation. Alternatively, the containment devices 602 can be introduced via oral ingestion by the patient or an intravenous therapy method.

Figure 17:
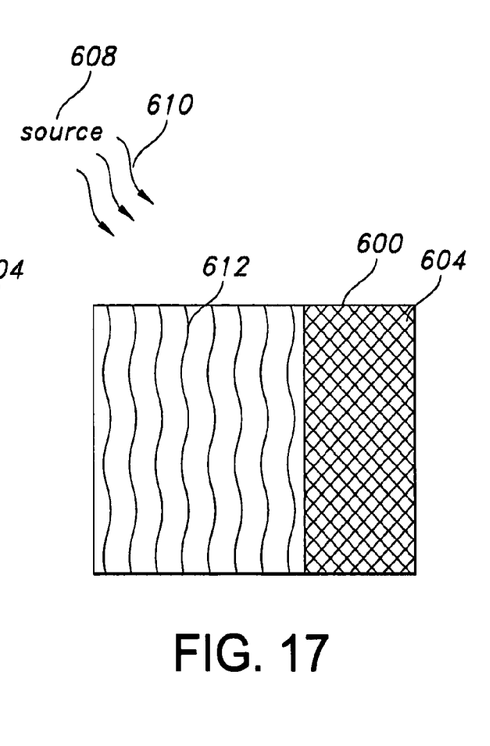
FIG. 17 illustrates the environment of FIG. 16 with medicament substantially released form the medicament containment devices.
Figure 18:
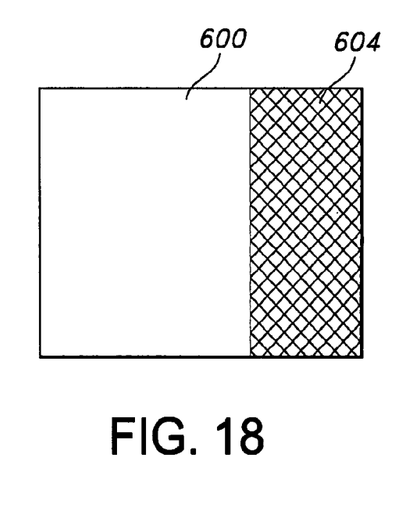
FIG. 18 illustrates the environment of FIG. 16 after the medicament is substantially released.

An energy source 608 is provided in FIG. 17 that can be used to apply energy 610 to the environment 600. Upon exposure to the energy 610, the containment devices 602 can substantially release a medicament 612 that kills or otherwise disrupts the bacteria colony 606. The result of releasing medicament 612 is shown in FIG. 18 as an implant 604 without a bacteria colony attached or otherwise surrounding the implant 604.

Medicament containment devices according to some embodiments of the present invention may be made from any type of material, one example of which is self healing polymers including bone cement. Specifically, microcapsules may be filled with a liquid monomer and dispersed in an epoxy matrix. A catalyst is embedded in the epoxy that induces polymerisation of the encapsulated monomer. When a crack occurs through the cured material, the micro-capsules are broken open. Capillary action draws the monomer into the crack and exposes it to the catalyst. The monomer then polymerises. The polymerised material then binds two faces of the crack together. Other material that may be used to make the containment devices includes titanium, titanium alloys, steel, cobalt-chromium alloys, tantalum, magnesium, peek, polyethylene, bioglass, brushite, hydroxy-appetite, calcium sulfate, calcium phosphate, silicon oxide, silk, poly-alpha-hydroxy acids, polyglycols, polytyrosine carbonates, starch, gelatins, polysaccharides, polyurethanes, polyesters, polyphosphoesters, polyphosphates, polyphosphonates, modified protein, polyorthoesters, trimethylenecarbonate, polydioxanones, polycapropactones, cellulose, polylactides, polyglycolic acid, copolymers, or any combination of the above or other material.

The following is an example of a medicament delivery system and method according to one embodiment of the present invention. Medicament containment devices may include an outer layer surrounding an inner layer that surrounds an antibiotic medicament. The outer layer is made from polyethlyene, forming a layer that can at least partially degrade upon exposure to energy, such as ultrasonic energy. The inner layer is made from polylactic acid (PLA) isomers, forming a resorbable layer that at least partially degrades upon exposure to body tissue. The containment devices may be made to any size. For example, the containment devices can have dimensions of 0.2 mm to 5 mm long with a width of 0.2 mm to 5 mm. In one particular embodiment, the containment devices are 2 mm long with a width of 1 mm.

A pool of containment devices is collected and a sterilized intermedullary plate orthopaedic implant is covered with an adhesive paste and dipped into the pool of containment devices. The containment devices are attached to the orthopaedic implant via the adhesive paste. Alternatively, the orthopaedic implant may be un-sterilized when dipped into the pool of containment devices and then the orthopaedic implant with attached containment devices is sterilized. After the adhesive paste solidifies, the orthopaedic implant is packaged into a vacuum pack with an insulation layer around the pack, at least in part, to prevent energy from degrading the containment devices prior to implantation. The pack is then stored until implantation.

In another example, medicament containment devices may be associated with the implant by electrostatically charging the implant to a positive or negative charge and a group of medicament containment devices to the opposite charge. The implant and medicament containment devices are then sintered by heating them to a temperature below or just at the melting point of the medicament containment devices and bringing them in proximity to each other. The medicament containment devices then attach to the implant.

An orthopedist removes the orthopaedic implant from the pack and implants it into a patients body. After a period of time, the patient may experience an infection around the orthopaedic implant caused by bacterial colonies forming around the orthopaedic implant and seek medical attention to treat the infection. The orthopedist, or other user, uses an ultrasound energy source, such as a low intensity ultrasound bone healing system manufactured by Exogen™, outside the patient's body but in relative proximity to the location of the orthopaedic implant to introduce ultrasound energy to the orthopaedic implant area. The ultrasound energy source includes a dial that allows the user to select a frequency at which to release the energy.

The containment devices with an outer layer having a resonant frequency at the frequency of the applied energy degrade after exposure to the energy and expose the resorbable inner layer to the patient's body tissue. The resonant frequency of each containment device can be controlled by the size and type of material that the containment devices are made from. For example, some of the containment devices may also be made from calcium phosphate at different levels to provide containment devices that degrade at different ultrasound frequencies. Over a period of time, the resorbable inner layer degrades due to exposure to the patient's body tissue and time-releases the antibiotic medicament into the patient's body. The antibiotic medicament kills all or at least part of the bacterial colonies.

If the bacterial colonies return after a period of time, a user selects a second energy frequency on the ultrasound energy source and applies energy at the selected frequency to the orthopaedic implant area. Containment device outer layers that did not degrade upon exposure to the first energy frequency, but have a resonant frequency at the second energy frequency, degrade to expose the resorbable inner layer to the patient's body tissue. The resorbable inner layer degrades over a period of time due to exposure to the patient's body tissue and substantially releases the antibiotic medicament within the inner layer. This process may be repeated as necessary.

The foregoing description of the embodiments, including example embodiments, of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of this invention.

What is claimed is:

1. A medicament containment device for association with an orthopaedic implant, the medicament containment device comprising:
    a first medicament;
    a second medicament; and
    a first layer substantially surrounding a second layer, the first medicament being disposed between the first layer and the second layer, and the second layer substantially surrounding the second medicament;
    wherein the medicament containment device is attached to or embedded in the orthopaedic implant;
    wherein the first layer is configured to at least partially degrade and release at least part of the first medicament in response to ultrasound energy from an energy source, the first layer at least partially exposing the second layer to an environment after the first layer at least partially degrades; and
    wherein the second layer is configured to at least partially degrade over time in response to exposure to the environment and release at least part of the second medicament over time in response to exposure to the environment after the first layer at least partially degrades.

2. The medicament containment device of claim 1, wherein the first layer has a first resonant frequency and is configured to degrade in response to energy at the first resonant frequency, and wherein the second layer has a second resonant frequency and is configured to degrade in response to energy at the second resonant frequency, the second resonant frequency being different from the first resonant frequency.

3. The medicament containment device of claim 1, wherein the orthopaedic implant is a resorbable orthopaedic implant configured to degrade over a period of time and the medicament is a resorbtion acceleration agent; and
    wherein the resorbtion acceleration agent is configured to increase the rate of degradation by the resorbable orthopaedic implant.

4. The medicament containment device of claim 1, wherein the energy is at least one of an ultrasound wave, thermal, light wave, radar, sonar, ultraviolet light wave, microwave, electrical, magnetic field, vibratory, and laser.

5. The medicament containment device of claim 1, wherein the first medicament or the second medicament comprises an antibiotic.

6. The medicament containment device of claim 1, wherein the first medicament or the second medicament comprises an osteogenic factor.

7. The medicament containment device of claim 1, wherein the first medicament or the second medicament comprises an osteoblast affecting agent or an osteoclast affecting agent.

8. A medicament containment device for association with an orthopaedic implant, the medicament containment device comprising:
    a medicament; and
    a first layer substantially surrounding a second layer, the second layer substantially surrounding the medicament;
    wherein the medicament containment device is attached to or embedded in the orthopaedic implant, the orthopaedic implant comprising a bone fixation structure;
    wherein the first layer is configured to at least partially degrade when the first layer is exposed to energy from an energy source;
    wherein the second layer is configured to at least partially degrade and release at least part of the medicament after the first layer degrades;
    wherein the orthopaedic implant is a resorbable orthopaedic implant configured to degrade over a period of time and the medicament is a resorbtion acceleration agent; and
    wherein the resorbtion acceleration agent is configured to increase the rate of degradation by the resorbable orthopaedic implant.

9. The medicament containment device of claim 8, wherein the first layer at least partially exposes the second layer to an environment; and wherein the second layer is a resorbable layer and is configured to at least partially degrade after exposure to the environment.

10. The medicament containment device of claim 8, wherein the first layer has a first resonant frequency and is configured to degrade in response to energy at the first resonant frequency, and wherein the second layer has a second resonant frequency and is configured to degrade in response to energy at the second resonant frequency, the second resonant frequency being different from the first resonant frequency.

11. The medicament containment device of claim 8, wherein the energy is at least one of an ultrasound wave, thermal, light wave, radar, sonar, ultraviolet light wave, microwave, electrical, magnetic field, vibratory, and laser.

12. A medicament containment device for association with an orthopaedic implant, the medicament containment device comprising:
    a medicament; and
    a first layer substantially surrounding a second layer, the second layer substantially surrounding the medicament;
    wherein the medicament containment device is attached to or embedded in the orthopaedic implant;
    wherein the first layer is configured to at least partially degrade when the first layer is exposed to ultrasound energy at a first frequency, wherein ultrasound energy at the first frequency does not cause degradation of the second layer sufficient to release the medicament; and
    wherein the second layer is configured to at least partially degrade and release at least part of the medicament in response to ultrasound energy at a second frequency after the first layer at least partially degrades, the second frequency being different from the first frequency.

13. The medicament containment device of claim 12, wherein the first layer at least partially exposes the second layer to an environment; and wherein the second layer is a resorbable layer and is configured to at least partially degrade after exposure to the environment.

14. The medicament containment device of claim 12, further comprising: a first medicament between the first layer and the second layer, wherein the medicament substantially surrounded by the second layer is a second medicament.

15. The medicament containment device of claim 12, wherein the orthopaedic implant is a resorbable orthopaedic implant configured to degrade over a period of time and the medicament is a resorbtion acceleration agent; and
   wherein the resorbtion acceleration agent is configured to increase the rate of degradation by the resorbable orthopaedic implant.

16. The medicament containment device of claim 14, wherein the first medicament or the second medicament comprises an antibiotic.

17. The medicament containment device of claim 14, wherein the first medicament or the second medicament comprises an osteogenic factor.

18. The medicament containment device of claim 14, wherein the first medicament or the second medicament comprises an osteoblast affecting agent or an osteoclast affecting agent.

19. The medicament containing device of claim 8, wherein the resorbable orthopaedic implant is an internal bone fixation device comprising a plate,
   wherein the medicament containing device is attached to or embedded in the plate, and
   wherein the medicament containing device is arranged on the plate to release the resorbtion acceleration agent to increase the rate of degradation of the plate.

20. The medicament containing device of claim 8, wherein the resorbable orthopaedic implant is an internal bone fixation device comprising an intramedullary nail,
   wherein the medicament containing device is attached to or embedded in the intramedullary nail, and
   wherein of the medicament containing device is arranged on the intramedullary nail to release the resorbtion acceleration agent to increase the rate of degradation of the intramedullary nail.

21. The medicament containing device of claim 12, wherein the medicament is a first medicament, and
   wherein the medicament containing device further comprises a second medicament disposed between the first layer and the second layer, the first layer being configured to release the first medicament after the first layer at least partially degrades in response to exposure to ultrasound energy at the first frequency.

* * * * *

UNITED STATES PATENT AND TRADEMARK OFFICE
CERTIFICATE OF CORRECTION

PATENT NO. : 9,849,216 B2
APPLICATION NO. : 12/281495
DATED : December 26, 2017
INVENTOR(S) : Gene Edward Austin et al.

It is certified that error appears in the above-identified patent and that said Letters Patent is hereby corrected as shown below:

In the Claims

At Column 14, Line 15 (Claim 20, Line 6), after "wherein", delete "of".

Signed and Sealed this
First Day of May, 2018

Andrei Iancu
*Director of the United States Patent and Trademark Office*